US012605106B2

(12) United States Patent
Hao et al.

(10) Patent No.: US 12,605,106 B2
(45) Date of Patent: Apr. 21, 2026

(54) ASSESSING PARKINSON'S DISEASE SYMPTOMS

(71) Applicant: INTERNATIONAL BUSINESS MACHINES CORPORATION, Armonk, NY (US)

(72) Inventors: Tian Hao, White Plains, NY (US); Jeffrey L. Rogers, Briarcliff Manor, NY (US); Umar Asif, Melbourne (AU); Erhan Bilal, Westport, CT (US); Deval Samirbhai Mehta, Melbourne (AU); Stefan Harrer, Hampton (AU); Jianbin Tang, Doncaster East (AU); Stefan von Cavallar, Sandringham (AU); Paolo Fraccaro, Warrington (GB)

(73) Assignee: International Business Machines Corporation, Armonk, NY (US)

( * ) Notice: Subject to any disclaimer, the term of this patent is extended or adjusted under 35 U.S.C. 154(b) by 332 days.

(21) Appl. No.: 17/249,412

(22) Filed: Mar. 2, 2021

(65) Prior Publication Data

US 2022/0280098 A1     Sep. 8, 2022

(51) Int. Cl.
*A61B 5/00* (2006.01)
*A61B 5/11* (2006.01)
*G16H 50/20* (2018.01)
*G16H 50/30* (2018.01)

(52) U.S. Cl.
CPC .......... *A61B 5/4082* (2013.01); *A61B 5/0004* (2013.01); *A61B 5/1101* (2013.01); *A61B 5/1116* (2013.01); *A61B 5/112* (2013.01);
*A61B 5/4803* (2013.01); *A61B 5/7267* (2013.01); *G16H 50/20* (2018.01); *G16H 50/30* (2018.01)

(58) Field of Classification Search
CPC ... A61B 5/4082; A61B 5/0004; A61B 5/1101; A61B 5/1116; A61B 5/112; A61B 5/4803; A61B 5/7267; G16H 50/20; G16H 50/30
See application file for complete search history.

(56) References Cited

U.S. PATENT DOCUMENTS

| | | | | |
|---|---|---|---|---|
| 9,706,962 B1 * | 7/2017 | Uehara | ................ | A61B 5/1107 |
| 9,877,680 B1 | 1/2018 | Giuffrida | | |
| 11,253,173 B1 * | 2/2022 | Demiralp | ............. | A61B 5/1122 |
| 11,363,982 B1 * | 6/2022 | Giuffrida | ............. | A61K 31/198 |

(Continued)

OTHER PUBLICATIONS

Perlmutter, Joel S. "Assessment of Parkinson disease manifestations." Current protocols in neuroscience vol. Chapter 10 (2009): Unit10.1. doi:10.1002/0471142301.ns1001s49 (Year: 2009).*

(Continued)

*Primary Examiner* — Justin Xu
*Assistant Examiner* — Jonathan M Haney
(74) *Attorney, Agent, or Firm* — Robert D. Bean

(57) ABSTRACT

The exemplary embodiments disclose a system and method, a computer program product, and a computer system for assessing one or more Parkinson's disease symptoms. The exemplary embodiments may include collecting data of a user's motion, extracting one or more features from the collected data, and assessing one or more Parkinson's disease symptoms of the user based on applying one or more models to the data.

20 Claims, 11 Drawing Sheets

(56) References Cited

U.S. PATENT DOCUMENTS

| | | | | |
|---|---|---|---|---|
| 2005/0197561 | A1* | 9/2005 | Elsinger | G01R 33/4806 |
| | | | | 600/410 |
| 2016/0022137 | A1 | 1/2016 | Wetzel | |
| 2017/0086712 | A1 | 3/2017 | Mauro | |
| 2017/0287146 | A1* | 10/2017 | Pathak | G16H 15/00 |
| 2017/0365101 | A1* | 12/2017 | Samec | G16H 20/70 |
| 2018/0338710 | A1 | 11/2018 | Tas | |
| 2019/0200914 | A1 | 7/2019 | Wagner | |
| 2020/0000373 | A1* | 1/2020 | Agrawal | A61B 5/7267 |
| 2020/0060602 | A1 | 2/2020 | Wagner | |
| 2021/0202091 | A1* | 7/2021 | Receveur | G16H 40/67 |

OTHER PUBLICATIONS

Asif et al., "DeepActsNet: Spatial and Motion features from Face, Hands, and Body Combined with Convolutional and Graph Networks for Improved Action Recognition." [Submitted on Sep. 21, 2020], https://arxiv.org/abs/2009.09818, pp. 1-9.

Bevilacqua et al., "A RGB-D Sensor Based Tool for Assessment and Rating of Movement Disorders." In: Duffy V., Lightner N. (eds) Advances in Human Factors and Ergonomics in Healthcare and Medical Devices. AHFE 2017. Advances in Intelligent Systems and Computing, vol. 590, 2018 Springer, pp. 110-118.

Ferraris et al., "Automated Assessment of Motor Impairments in Parkinson's Disease," The Clinical Neurologist International, vol. 1, article 1009, 2020, pp. 28-31.

Ferraris et al., "Feasibility of home-based automated assessment of postural instability and lower limb impairments in Parkinson's disease." Sensors, 19(5), 1129, 2019, pp. 1-21.

Goetz et al., "MDS-Unified Parkinson's Disease Rating Scale (MDS-UPDRS)", https://www.movementdisorders.org/MDS/MDS-Rating-Scales/MDS-Un . . . , accessed Mar. 2, 2021, pp. 1-5.

https://www.michaeljfox.org/news/medications-motor-symptoms, "Medications for Motor Symptoms", Parkinson's Disease, accessed Mar. 2, 2021, pp. 1-7.

Lin et al., "Bradykinesia Recognition in Parkinson's Disease via Single RGB Video." ACM Trans. Knowl. Discov. Data 14, 2, Article 16, Mar. 2020, pp. 1-19.

Lu et al., "Vision-based Estimation of MDS-UPDRS Gait Scores for Assessing Parkinson's Disease Motor Severity," Med Image Computing Computer-Assist Interv., 12263: Oct. 2020, 1129; doi:10.3390/s19051129, pp. 1-14.

Mell et al., "The NIST Definition of Cloud Computing", National Institute of Standards and Technology, Special Publication 800-145, Sep. 2011, pp. 1-7.

* cited by examiner

100

ASSESSING PARKINSON'S DISEASE SYMPTOMS

BACKGROUND

The exemplary embodiments relate generally to assessing disease symptoms, and more particularly to assessing Parkinson's disease symptoms by collecting and analyzing data.

Parkinson's disease is a neurological condition that affects millions of individuals worldwide with symptoms of tremors, slowness of movement, muscular rigidity, and gait and balance disturbances, among others. The Unified Parkinson's Disease Rating Scale (UPDRS) includes a Postural Instability and Gait Disturbance (PIGD) test, which is often used by medical professionals to score a patient's gait and postural deficits on a scale of 0 to 4. The PIGD test is highly subjective and has poor correlation and consistency between different medical professionals. It can therefore be very difficult for medical professionals to objectively assess the severity of Parkinson's disease symptoms.

When an automated system is used to assess Parkinson's disease symptoms, the automated system may utilize various detection or assessment techniques. However, conventional approaches often solely use an image capture device in a general manner, solely utilize on-body motion sensors, or solely utilize eye-tracking sensors to assess Parkinson's disease symptoms.

U.S. Publ. Appln. No. 2019/0200914A1 describes a conventional approach wherein motion is analyzed in general based on motion data derived from an image capture device. U.S. Pat. No. 98,776,680B1 describes a conventional approach wherein on-body motion sensors are used to monitor Parkinson's disease symptoms. U.S. Publ. Appln. No. 2016/0022137A1 describes a conventional approach wherein eye movement from an eye tracker is used to monitor Parkinson's disease symptoms.

These conventional approaches are only generally indicative of Parkinson's disease symptoms at best, as they do not directly assess individual UPDRS tasks.

SUMMARY

The exemplary embodiments disclose a system and method, a computer program product, and a computer system for assessing one or more Parkinson's disease symptoms. The exemplary embodiments may include collecting data of a user's motion, extracting one or more features from the collected data, and assessing one or more Parkinson's disease symptoms of the user based on applying one or more models to the data.

In a preferred embodiment, the user and a medical professional are notified of the assessed one or more Parkinson's disease symptoms.

In a preferred embodiment, the one or more models correlate the one or more features with one or more assessments of Parkinson's disease symptoms.

In a preferred embodiment, feedback is received indicative of whether the assessment of one or more Parkinson's disease symptoms was accurate, and the one or more models are adjusted based on the received feedback.

In a preferred embodiment, training data is collected, training features are extracted from the training data, and the one or more models are trained based on the extracted training features.

In a preferred embodiment, assessing one or more Parkinson's disease symptoms of the user comprises an assessment of the user's speech, facial expression, rigidity, finger tapping, hand movements, rapid alternating movements of hands, toe tapping, leg agility, arising from chair, gait, freezing of gait, postural stability, posture, body bradykinesia, postural tremor of hands, kinetic tremor of hands, rest tremor amplitude of extremities, rest tremor amplitude of lip and jaw, and constancy of tremor.

In a preferred embodiment, the one or more features include features selected from a group comprising degree of facial expression, degree of lips parted, amplitude of motion, speed of motion, hesitation, assistance needed, arm swing, short steps, posture stability, and amplitude of tremor.

BRIEF DESCRIPTION OF THE SEVERAL VIEWS OF THE DRAWINGS

The following detailed description, given by way of example and not intended to limit the exemplary embodiments solely thereto, will best be appreciated in conjunction with the accompanying drawings, in which.

The drawings are not necessarily to scale. The drawings are merely schematic representations, not intended to portray specific parameters of the exemplary embodiments. The drawings are intended to depict only typical exemplary embodiments. In the drawings, like numbering represents like elements.

DETAILED DESCRIPTION OF THE SEVERAL VIEWS OF THE DRAWINGS

Figure 1:
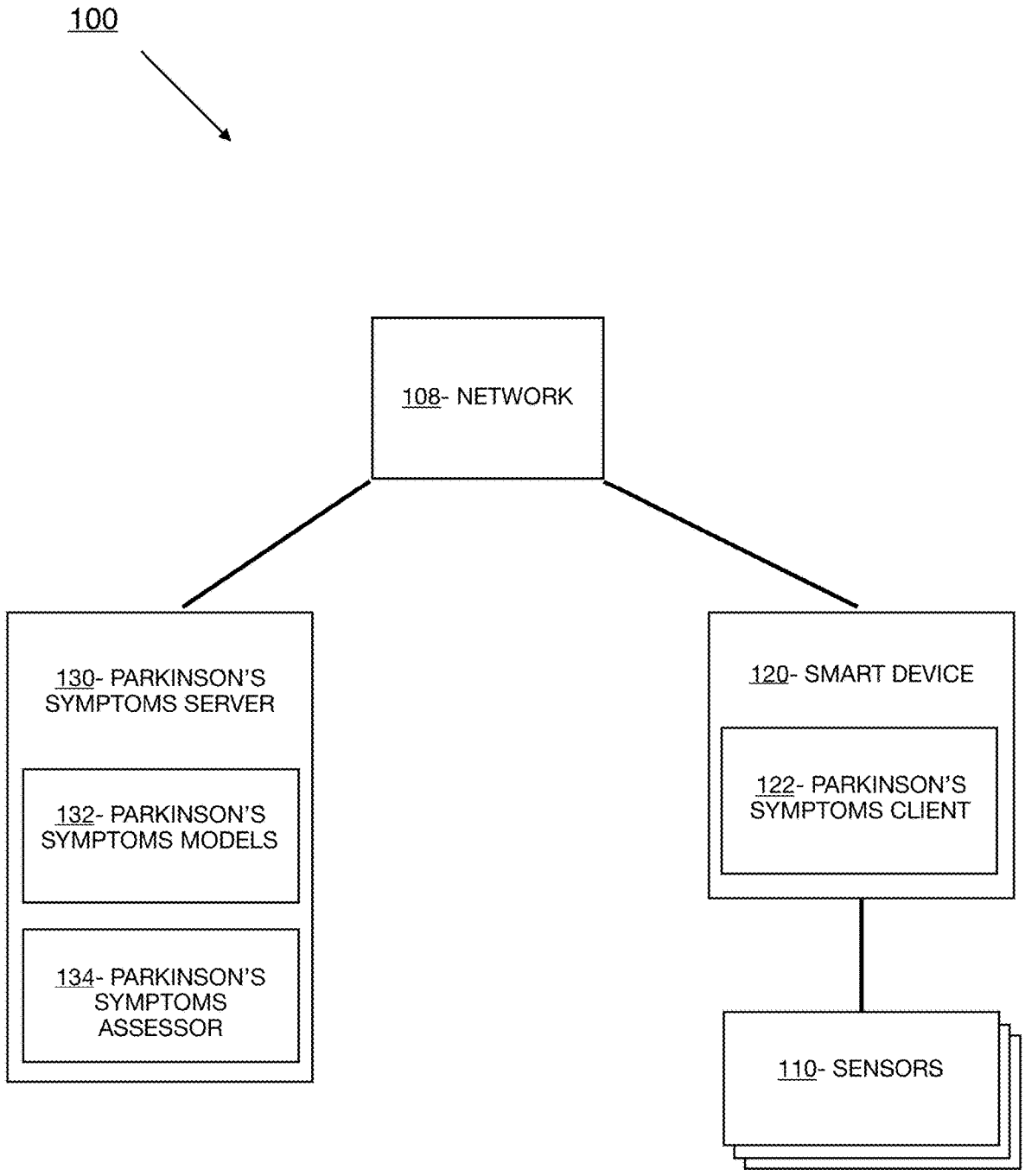
FIG. 1 depicts an exemplary schematic diagram of a Parkinson's symptoms system 100, in accordance with the exemplary embodiments.

Detailed embodiments of the claimed structures and methods are disclosed herein; however, it can be understood that the disclosed embodiments are merely illustrative of the claimed structures and methods that may be embodied in various forms. The exemplary embodiments are only illustrative and may, however, be embodied in many different forms and should not be construed as limited to the exemplary embodiments set forth herein. Rather, these exemplary embodiments are provided so that this disclosure will be thorough and complete, and will fully convey the scope to be covered by the exemplary embodiments to those skilled in the art. In the description, details of well-known features and techniques may be omitted to avoid unnecessarily obscuring the presented embodiments.

References in the specification to "one embodiment", "an embodiment", "an exemplary embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to implement such feature, structure, or characteristic in connection with other embodiments whether or not explicitly described.

In the interest of not obscuring the presentation of the exemplary embodiments, in the following detailed description, some processing steps or operations that are known in the art may have been combined together for presentation and for illustration purposes and in some instances may have not been described in detail. In other instances, some processing steps or operations that are known in the art may not be described at all. It should be understood that the following description is focused on the distinctive features or elements according to the various exemplary embodiments.

Parkinson's disease is a neurological condition that affects millions of individuals worldwide with symptoms of tremors, slowness of movement, muscular rigidity, and gait and balance disturbances, among others. The Unified Parkinson's Disease Rating Scale (UPDRS) includes a Postural Instability and Gait Disturbance (PIGD) test, which is often used by medical professionals to score a patient's gait and postural deficits on a scale of 0 to 4. The PIGD test is highly subjective and has poor correlation and consistency between different medical professionals. It can therefore be very difficult for medical professionals to objectively assess the severity of Parkinson's disease symptoms.

Exemplary embodiments are directed to a method, computer program product, and computer system that will assess Parkinson's disease symptoms. In embodiments, machine learning may be used to create models capable of assessing Parkinson's disease symptoms such as speech, facial expression, rigidity, finger tapping, hand movements, rapid alternating movements of hands, toe tapping, leg agility, arising from chair, gait, freezing of gait, postural stability, posture, body bradykinesia, postural tremor of hands, kinetic tremor of hands, rest tremor amplitude of extremities, rest tremor amplitude of lip and jaw, constancy of tremor, etc., while feedback loops may improve upon such models. Moreover, data from sensors, the internet, and user profiles may be utilized to collect data for symptoms assessments. The various data may be indicative of features such as degree of facial expression, degree of lips parted, amplitude of motion, speed of motion, hesitation, assistance needed, arm swing, short steps, posture stability, amplitude of tremor, etc. In general, it will be appreciated that embodiments described herein may relate to aiding in the assessment of any Parkinson's disease symptoms of any humans within any environment and for any motivation.

FIG. 1 depicts the Parkinson's symptoms system 100, in accordance with the exemplary embodiments. According to the exemplary embodiments, the Parkinson's symptoms system 100 may include a smart device 120 and a Parkinson's symptoms server 130, which may be interconnected via a network 108. While programming and data of the exemplary embodiments may be stored and accessed remotely across several servers via the network 108, programming and data of the exemplary embodiments may alternatively or additionally be stored locally on as few as one physical computing device or amongst other computing devices than those depicted.

In the exemplary embodiments, the network 108 may be a communication channel capable of transferring data between connected devices. Accordingly, the components of the Parkinson's symptoms system 100 may represent network components or network devices interconnected via the network 108. In the exemplary embodiments, the network 108 may be the Internet, representing a worldwide collection of networks and gateways to support communications between devices connected to the Internet. Moreover, the network 108 may utilize various types of connections such as wired, wireless, fiber optic, etc. which may be implemented as an intranet network, a local area network (LAN), a wide area network (WAN), or a combination thereof. In further embodiments, the network 108 may be a Bluetooth network, a Wi-Fi network, or a combination thereof. In yet further embodiments, the network 108 may be a telecommunications network used to facilitate telephone calls between two or more parties comprising a landline network, a wireless network, a closed network, a satellite network, or a combination thereof. In general, the network 108 may represent any combination of connections and protocols that will support communications between connected devices.

In the example embodiment, the smart device 120 includes a Parkinson's symptoms client 122 and may be an enterprise server, a laptop computer, a notebook, a tablet computer, a netbook computer, a personal computer (PC), a desktop computer, a server, a personal digital assistant (PDA), a rotary phone, a touchtone phone, a smart phone, a mobile phone, a virtual device, a thin client, an IoT device, or any other electronic device or computing system capable of receiving and sending data to and from other computing devices. While the smart device 120 is shown as a single device, in other embodiments, the smart device 120 may be comprised of a cluster or plurality of computing devices, in a modular manner, etc., working together or working independently. The smart device 120 is described in greater detail as a hardware implementation with reference to FIG. 9, as part of a cloud implementation with reference to FIG. 10, and/or as utilizing functional abstraction layers for processing with reference to FIG. 11.

The Parkinson's symptoms client 122 may be a software and/or hardware application capable of communicating with and providing a user interface for a user to interact with a server via the network 108. The Parkinson's symptoms client 122 may act as a client in a client-server relationship. Moreover, in the example embodiment, the Parkinson's symptoms client 122 may be capable of transferring data between the smart device 120 and the Parkinson's symptoms server 130 via the network 108. In embodiments, the Parkinson's symptoms assessor 134 utilizes various wired and wireless connection protocols for data transmission and exchange, including Bluetooth, 2.4 gHz and 5 gHz internet, near-field communication, Z-Wave, Zigbee, etc. The Parkinson's symptoms client 122 is described in greater detail with respect to FIG. 2.

In the exemplary embodiments, the one or more sensors 110 may be a camera, accelerometer, gyroscope, compass, microphone, light sensor, infrared sensor, movement detection sensor, pressure sensor, or other sensory hardware/software equipment. In embodiments, the sensors 110 may be integrated with and communicate directly with the smart device 120, e.g., smart phones and laptops. Although the sensors 110 are depicted as external to the smart device 120, in embodiments, the sensors 110 may be integrated within smart device 120 or connected to the smart device 120 or the network 108. In embodiments, the sensors 110 may be incorporated within an environment in which the Parkinson's symptoms system 100 is implemented. For example, the sensors 110 may include a series of video cameras fastened to the walls of a medical facility. The sensors 110 are described in greater detail with respect to FIG. 2 and FIG. 9-11.

In the exemplary embodiments, the Parkinson's symptoms server 130 includes one or more Parkinson's symptoms models 132 and a Parkinson's symptoms assessor 134. The Parkinson's symptoms server 130 may act as a server in a client-server relationship with the Parkinson's symptoms client 122, and may be an enterprise server, a laptop computer, a notebook, a tablet computer, a netbook computer, a PC, a desktop computer, a server, a PDA, a rotary phone, a touchtone phone, a smart phone, a mobile phone, a virtual device, a thin client, an IoT device, or any other electronic device or computing system capable of receiving and sending data to and from other computing devices. While the Parkinson's symptoms server 130 is shown as a single device, in other embodiments, the Parkinson's symptoms server 130 may be comprised of a cluster or plurality of computing devices, working together or working independently. The Parkinson's symptoms server 130 is described in greater detail as a hardware implementation with reference to FIG. 9, as part of a cloud implementation with reference to FIG. 10, and/or as utilizing functional abstraction layers for processing with reference to FIG. 11.

The Parkinson's symptoms models 132 may be one or more algorithms modelling a correlation between one or more features and one or more assessments of Parkinson's disease symptoms. The one or more features may include features such as degree of facial expression, degree of lips parted, amplitude of motion, speed of motion, hesitation, assistance needed, arm swing, short steps, posture stability, amplitude of tremor, etc., and may be detected and extracted via the one or more sensors 110 and the network 108. In embodiments, the Parkinson's symptoms models 132 may weight the features based on an effect that the one or more features have on one or more assessments of Parkinson's disease symptoms. Assessments of Parkinson's disease symptoms may include assessments of speech, facial expression, rigidity, finger tapping, hand movements, rapid alternating movements of hands, toe tapping, leg agility, arising from chair, gait, freezing of gait, postural stability, posture, body bradykinesia, postural tremor of hands, kinetic tremor of hands, rest tremor amplitude of extremities, rest tremor amplitude of lip and jaw, constancy of tremor, etc. In the example embodiment, the Parkinson's symptoms assessor 134 may generate the Parkinson's symptoms models 132 using machine learning methods, such as neural networks, deep learning, hierarchical learning, Gaussian Mixture modelling, Hidden Markov modelling, and K-Means, K-Medoids, or Fuzzy C-Means learning, etc. The Parkinson's symptoms models 132 are described in greater detail with reference to FIG. 2.

The Parkinson's symptoms assessor 134 may be a software and/or hardware program capable of collecting training data, extracting features from the training data, and training one or more models based on the extracted features. The Parkinson's symptoms assessor 134 may also receive a configuration of the Parkinson's symptoms system 100, collect data of one or more users, extract features from the collected data, and apply the one or more models to make one or more Parkinson's symptoms assessments. In addition, the Parkinson's symptoms assessor 134 may be further configured to notify one or more users of the one or more assessments and modify the one or more models. The Parkinson's symptoms assessor 134 is described in greater detail with reference to FIG. 2.

Figure 2:
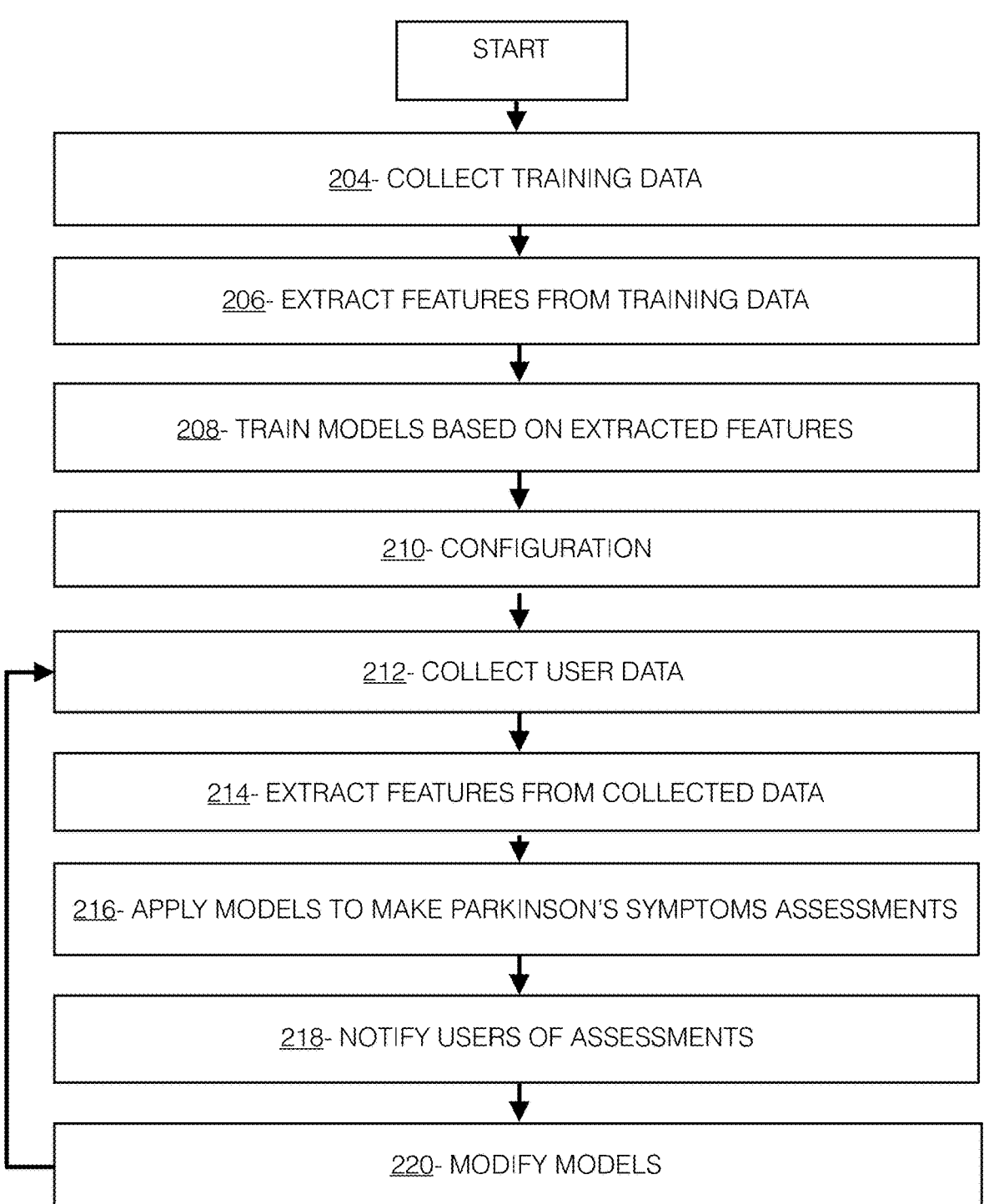
FIG. 2-3 depict exemplary flowcharts illustrating the operations of a Parkinson's symptoms assessor 134 of the Parkinson's symptoms system 100 in assessing Parkinson's disease symptoms, in accordance with the exemplary embodiments.

FIG. 2 depicts an exemplary flowchart illustrating the operations of a Parkinson's symptoms assessor 134 of the Parkinson's symptoms system 100 in assessing a user's gait, in accordance with the exemplary embodiments. In exemplary embodiments, the Parkinson's symptoms assessor 134 first implements a training phase in which it trains the Parkinson's symptoms models 132 using training data including various input data (i.e., video of users' movements, information from medical databases) and associated Parkinson's disease symptoms assessments. The Parkinson's symptoms assessor 134 then moves on to an operational phase in which it applies the trained Parkinson's symptoms models 132 to current user data in order to appropriately assess the user's Parkinson's disease symptoms.

Figure 3:
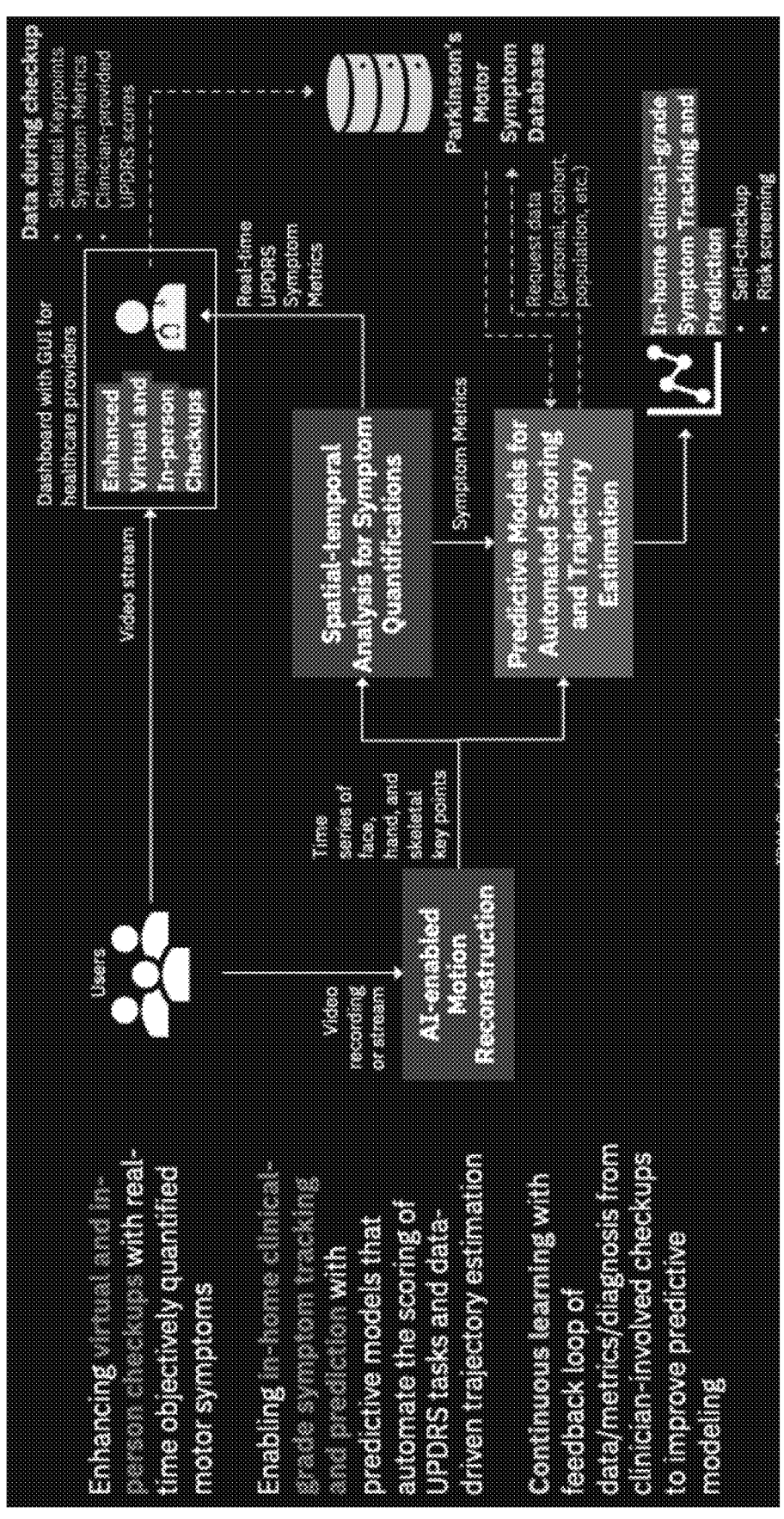
Figure 6:
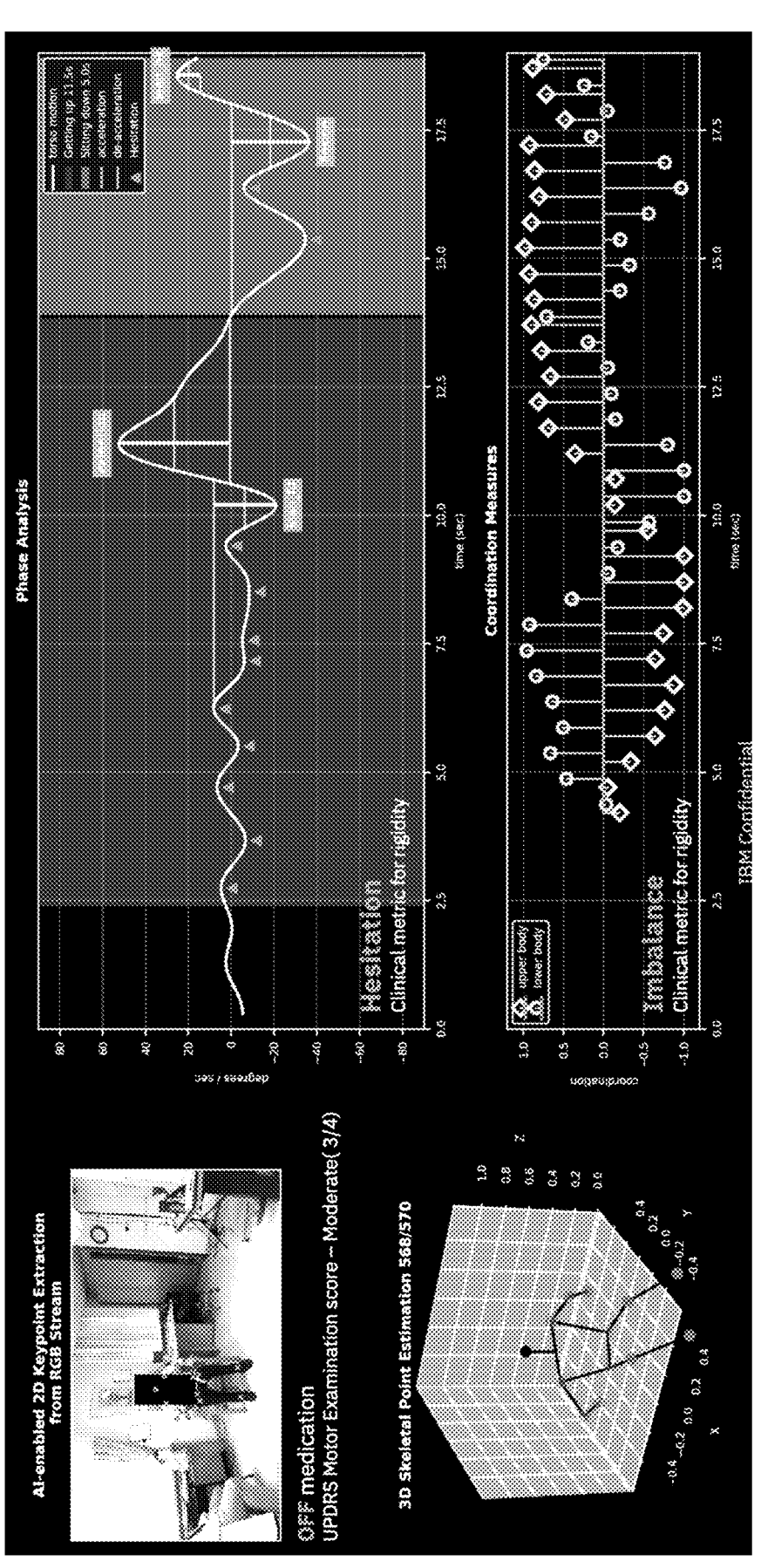
Figure 7:
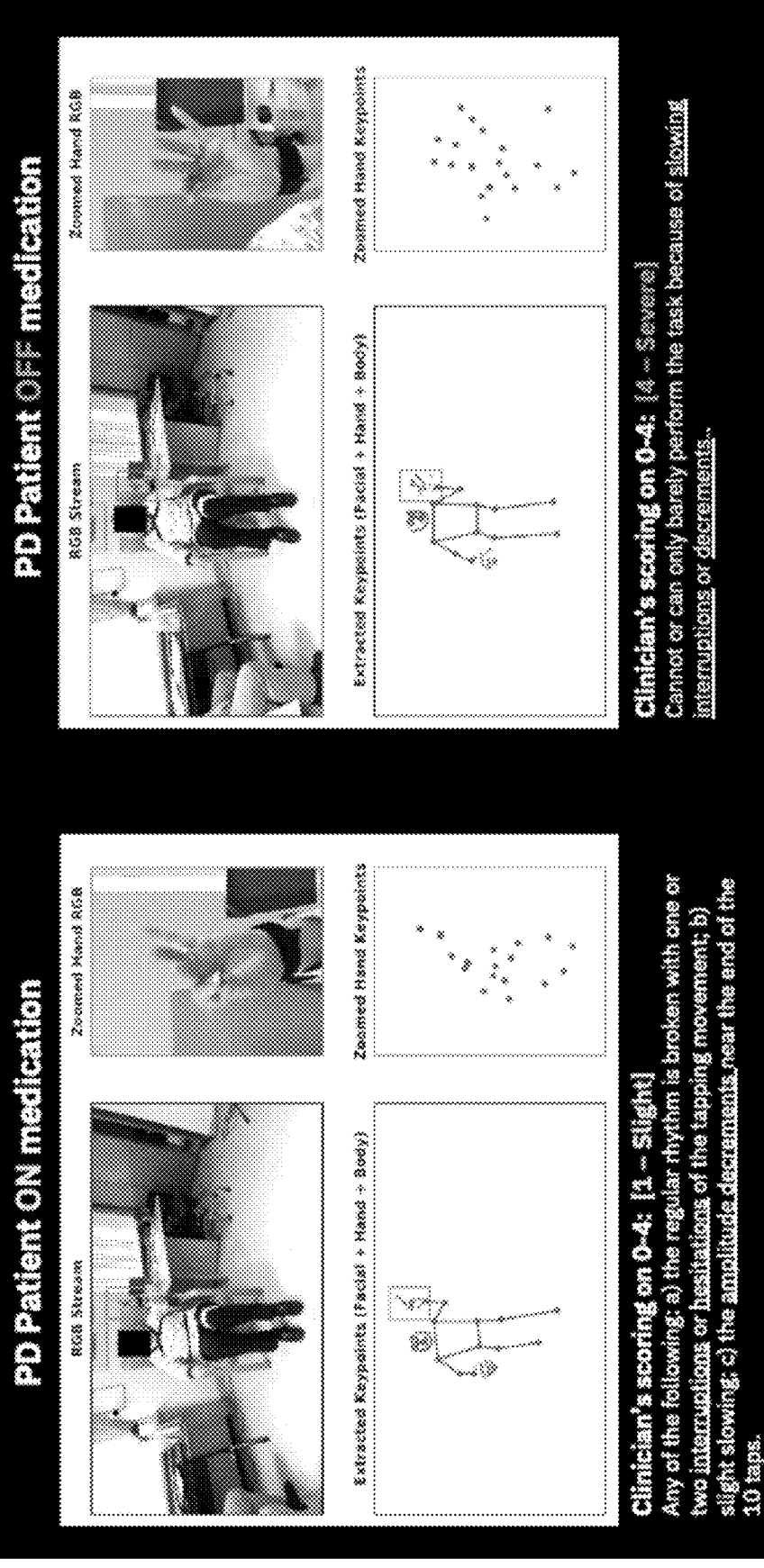

The Parkinson's symptoms assessor 134 may collect training data (step 204). In embodiments, the Parkinson's symptoms assessor 134 may collect training data via user upload, from databases, or from the sensors 110. With reference to FIG. 6, training data may be in any form representing an individual's motion, for example, a graph of degrees/sec over time (as depicted in FIG. 6), a graph of coordination over time (as depicted in FIG. 6), a graph of acceleration over time, a graph of gyration over time, tables, charts, lists, etc. In preferred embodiments, and as illustrated by FIG. 3, the training data is collected as one or more video streams or footage from video camera sensors 110 as an individual moves. With reference to FIG. 7, the training data may be received for one or more assessments of Parkinson's disease symptoms, for example baseline training data may be received for healthy individuals who have not been diagnosed with Parkinson's disease (healthy patient), individuals who have been diagnosed with Parkinson's disease but have mild symptoms due to taking medication (PD Patient ON), and individuals who have been diagnosed with Parkinson's disease and who exhibit worsening symptoms, for example due to their medication wearing off (PD Patient OFF). In embodiments, training data for additional or different assessments or classifications of individuals may be collected, for example, individuals who have been diagnosed with Parkinson's disease and exhibit symptoms that are 0-4 on the UPDRS. Upon receiving training data, the Parkinson's symptoms assessor 134 may process the collected raw training data. In embodiments, the Parkinson's symptoms assessor 134 may process the collected training data via amplification, filtering, and performing other data refining operations on the data. In embodiments where collected training data is in the form of video, and with reference to FIG. 6-7, the Parkinson's symptoms assessor 134 may first process the video with AI-enabled motion reconstruction. The Parkinson's symptoms assessor 134 may utilize a pipeline of pre-trained Deep learning Neural Networks to detect one or more individuals captured in each frame of the video as well as identify skeletal, facial and hand key points. The resulting time series of key points in 2D and/or 3D space representing human motion may then be processed or smoothed using linear trend fitting (e.g., using a window of 0.2 seconds) to filter out noise and to fill in any missing key points. The smoothed sequence of key points may be further processed to produce mobility or symptom-related features such as amplitude, coordination, postural stability, hesitation, etc. The Parkinson's symptoms assessor 134 may further apply a band filter or linear trend fitting to the training data to remove high frequency noise and the effect of gravity on an individual's movement. The data may further be processed by applying the Fast Fourier Transform (FFT) to each time series and keeping the resulting FFT amplitudes as features. In general, the Parkinson's symptoms assessor 134 may implement any data refining and processing operations in order to prepare the data for feature extraction.

To further illustrate the operations of the Parkinson's symptoms assessor 134, reference is now made to an illustrative example where the Parkinson's symptoms assessor 134 collects training data consisting of various patient movement data associated with Parkinson's disease symptoms assessments from 0-4 on the UPDRS.

The Parkinson's symptoms assessor 134 may extract one or more features from the collected and/or received training data (step 206). The extracted features may be extracted from the collected training data, which may be collected via user upload, databases, or the sensors 110, and may include features such as degree of facial expression, degree of lips parted, amplitude of motion, speed of motion, hesitation, assistance needed, arm swing, short steps, posture stability, amplitude of tremor, etc. In embodiments, the Parkinson's symptoms assessor 134 may use techniques such as feature extraction, optical character recognition, image processing, video processing, pattern/template matching, data comparison, etc. to identify features. For example, with reference to FIG. 4-7, the Parkinson's symptoms assessor 134 may use feature extraction, image processing, and video processing to extract features from collected video of an individual moving their face, hands, and/or other body parts (skeletal keypoint extraction shown in FIG. 4-7). With reference to FIG. 6-7, the Parkinson's symptoms assessor 134 may identify locations of one or more facial features, hands, skeletal keypoints (i.e., shoulders, elbows, wrists, hips, knees, ankles, etc.) across a period of time from the collected video of the individual moving. The Parkinson's symptoms assessor 134 may then extract features such as degree of facial expression, degree of lips parted, amplitude of motion, speed of motion, hesitation, assistance needed, arm swing, short steps, posture stability, amplitude of tremor, etc. from the analysis of collected video. In embodiments, the Parkinson's symptoms assessor 134 may extract these features as a rating (i.e., low, medium, high) or number representing severity (i.e., 0-10, 0-5, etc.) The Parkinson's symptoms assessor 134 may later associate extracted features with associated Parkinson's disease symptoms assessments when training one or more models.

With reference to the previously introduced example where the Parkinson's symptoms assessor 134 collects training data consisting of various patient movement data associated with Parkinson's disease symptoms assessments from 0-4 on the UPDRS, the Parkinson's symptoms assessor 134 extracts features degree of facial expression, degree of lips parted, amplitude of motion, speed of motion, hesitation, assistance needed, arm swing, short steps, posture stability, and amplitude of tremor from the collected training data.

Figure 8:
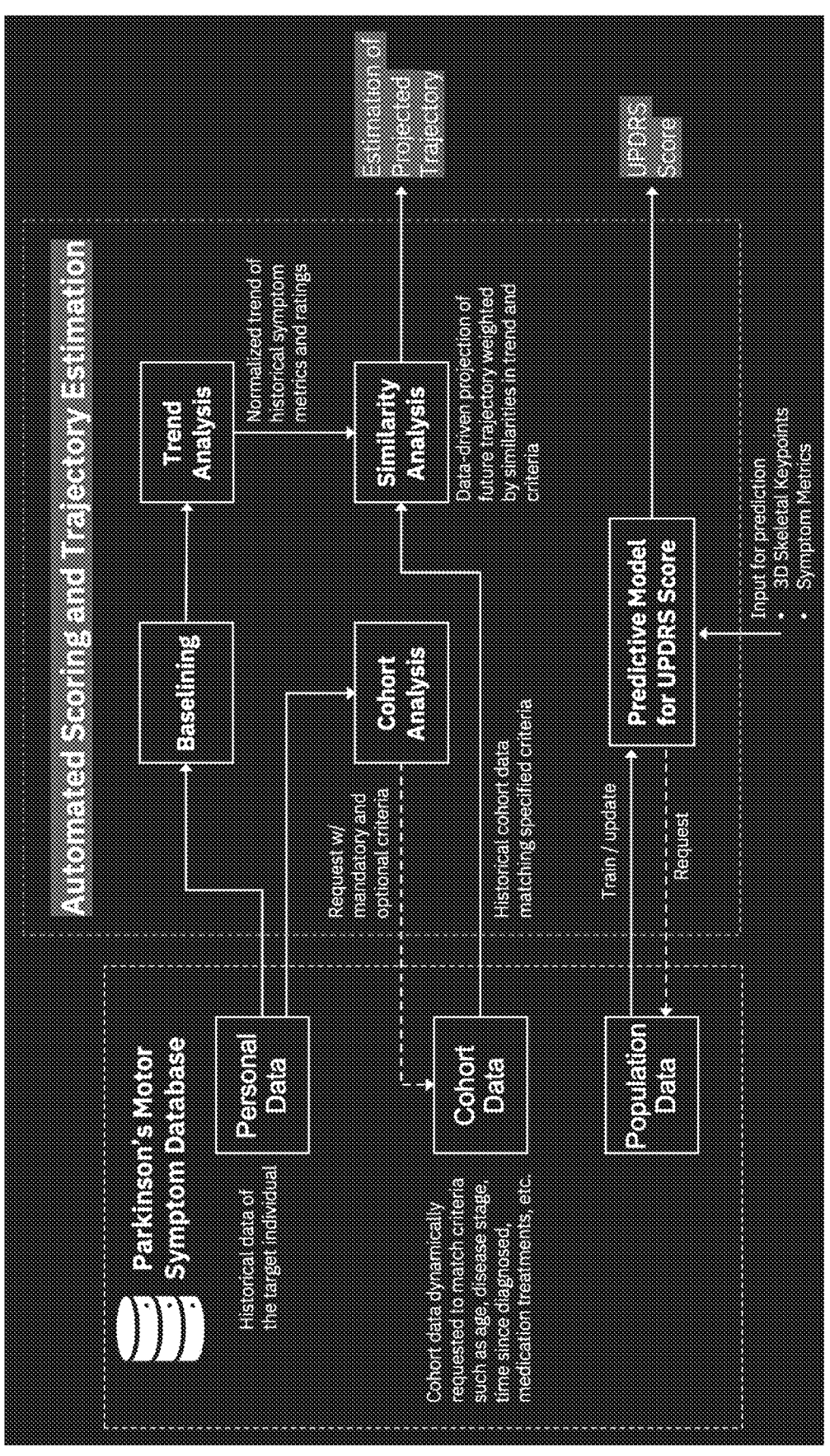
FIG. 8 depicts an exemplary flowchart illustrating the operations of a Parkinson's symptoms assessor 134 of the Parkinson's symptoms system 100 in collecting training data, extracting features from the collected training data, and training models based on the extracted features, in accordance with the exemplary embodiments.

The Parkinson's symptoms assessor 134 may train one or more Parkinson's symptoms models 132 based on the extracted features (step 208). The Parkinson's symptoms models 132 may be one or more algorithms modelling a correlation between one or more features of the training data and one or more Parkinson's disease symptoms assessments, such as speech, facial expression, rigidity, finger tapping, hand movements, rapid alternating movements of hands, toe tapping, leg agility, arising from chair, gait, freezing of gait, postural stability, posture, body bradykinesia, postural tremor of hands, kinetic tremor of hands, rest tremor amplitude of extremities, rest tremor amplitude of lip and jaw, constancy of tremor, etc. (i.e., making a numerical assessment of each symptom). In embodiments, Parkinson's disease symptoms assessments may be assessed on a scale of 0-4 (i.e., UPDRS) for each symptom. In embodiments, the Parkinson's symptoms models 132 may weight the features based on an effect that the one or more features have on the one or more Parkinson's symptoms assessments. In embodiments, the Parkinson's symptoms assessor 134 may generate the Parkinson's symptoms models 132 using machine learning methods, such as neural networks, deep learning, hierarchical learning, Gaussian Mixture modelling, Hidden Markov modelling, and K-Means, K-Medoids, or Fuzzy C-Means learning, etc. In the example embodiment, and with reference to FIG. 5, the Parkinson's symptoms assessor 134 may train one model for each type of Parkinson's disease symptom that is to be assessed (i.e. predictive model for finger tapping, and predictive model for arising from chair shown in FIG. 5). With reference to FIG. 8, the Parkinson's symptoms assessor 134 may additionally or alternatively train one model for each user or individual of the collected training data.

With reference again to the previously introduced example where the Parkinson's symptoms assessor 134 extracts features degree of facial expression, degree of lips parted, amplitude of motion, speed of motion, hesitation, assistance needed, arm swing, short steps, posture stability, and amplitude of tremor from the collected training data, the Parkinson's symptoms assessor 134 trains a model for each of the following Parkinson's disease symptoms: speech, facial expression, rigidity, finger tapping, hand movements, rapid alternating movements of hands, toe tapping, leg agility, arising from chair, gait, freezing of gait, postural stability, posture, body bradykinesia, postural tremor of hands, kinetic tremor of hands, rest tremor amplitude of extremities, rest tremor amplitude of lip and jaw, and constancy of tremor.

The Parkinson's symptoms assessor 134 may receive a configuration (step 210). The Parkinson's symptoms assessor 134 may be configured by receiving information such as a user registration and user preferences. The user registration may be uploaded by a user, i.e., the owner of the Parkinson's symptoms system 100, user of the Parkinson's symptoms system 100, a medical professional who oversees the usage of the Parkinson's symptoms system 100, a guardian of a minor who uses the Parkinson's symptoms system 100, an employer who oversees the usage of the Parkinson's symptoms system 100, etc. In the example embodiment, the user refers to the person for whom Parkinson's disease symptoms are being assessed, and the configuration may be received by the Parkinson's symptoms assessor 134 via the Parkinson's symptoms client 122 and the network 108. Receiving the user registration may involve referencing a user profile via user login credentials, internet protocol (IP) address, media access control (MAC) address, etc., or receiving user input information such as a name, date of birth, gender, address/geographic information, phone number, email address, company name, device serial number, smart device 120 type, and the like. Receiving a user registration may also involve receiving health data via user input or reference to an electronic medical/health record that includes data relevant to general user health, medical conditions, medications prescribed to the user, information about past medical office visits, information about primary care physicians, etc. Lastly, the Parkinson's symptoms assessor 134 may receive a configuration of the one or more sensors 110, whether they be fixed to the user (e.g., the smart device 120) or fixed within an environment in which the Parkinson's symptoms system 100 is implemented.

During configuration, the Parkinson's symptoms assessor 134 may further receive user preferences (step 210 continued). User preferences may include preferences for the manner in which the Parkinson's symptoms assessor 134 should notify one or more users of a Parkinson's disease symptoms assessment. For example, a user may upload user preferences specifying that they are to be notified of all Parkinson's disease symptoms assessments via visual notification on their smart device 120. In embodiments, user preferences may additionally specify that upon notification of a user and that user's confirmation, the Parkinson's symptoms assessor 134 is to notify one or more doctors, nurses, healthcare providers, etc. of the user. For example, if the Parkinson's symptoms assessor 134 notifies the user of severe worsening symptoms and the user approves the notification of their doctor, the Parkinson's symptoms assessor 134 may notify the user's doctor of the assessment. In embodiments, user preferences may be configured alternatively.

With reference again to the previously introduced example where the Parkinson's symptoms assessor 134 trains a model for many Parkinson's disease symptoms, the user uploads a user registration including the user's name, user's doctor's name, user's doctor's contact information, user's computer as smart device 120, and user's video cameras as sensors 110. The user also uploads user preferences specifying that notification of Parkinson's disease assessments are to be communicated to the user via visual notification on their computer smart device 120, and communicated to the user's doctor via visual notification on the doctor's smart device.

The Parkinson's symptoms assessor 134 may collect user data (step 212). In embodiments, the Parkinson's symptoms assessor 134 may collect user data via user upload, from databases, or from the sensors 110. With reference to FIG. 6, user data may be in any form representing an individual's motion, for example, a graph of degrees/sec over time (depicted in FIG. 6), a graph of coordination over time (depicted in FIG. 6), a graph of acceleration over time, a graph of gyration over time, tables, charts, lists, etc. In preferred embodiments, and as illustrated by FIG. 3, the user data is collected as one or more video streams or footage from video camera sensors 110 as an individual moves. Upon receiving user data, the Parkinson's symptoms assessor 134 may process the collected user data. In embodiments, the Parkinson's symptoms assessor 134 may process the collected user data via amplification, filtering, and performing other data refining operations on the data. In embodiments where collected user data is in the form of video, and with reference to FIG. 6-7, the Parkinson's symptoms assessor 134 may first process the video with AI-enabled motion reconstruction. The Parkinson's symptoms assessor 134 may utilize a pipeline of pre-trained Deep learning Neural Networks to detect one or more individuals captured in each frame of the video as well as identify skeletal, facial and hand key points. The resulting time series of key points in 2D and/or 3D space representing human motion may then be processed or smoothed using linear trend fitting (e.g., using a window of 0.2 seconds) to filter out noise and to fill in any missing key points. The smoothed sequence of key points may be further processed to produce mobility or symptom-related features such as amplitude, coordination, postural stability, hesitation, etc. The Parkinson's symptoms assessor 134 may further apply a band filter or linear trend fitting to the training data to remove high frequency noise and the effect of gravity on an individual's movement. The data may further be processed by applying the Fast Fourier Transform (FFT) to each time series and keeping the resulting FFT amplitudes as features. In general, the Parkinson's symptoms assessor 134 may implement any data refining and processing operations in order to prepare the data for feature extraction.

With reference again to the previously introduced example where the Parkinson's symptoms assessor 134 receives a user registration and user preferences, the Parkinson's symptoms assessor 134 collects user data from the sensors 110 of the user moving their face, hands, shoulders, elbows, hips, knees, and ankles.

The Parkinson's symptoms assessor 134 may extract one or more features from the collected user data (step 214). The Parkinson's symptoms assessor 134 may extract one or more features from the collected user data in the same manner as described above with respect to extracting features from the training data. However, the Parkinson's symptoms assessor 134 extracts one or more features from the current collected user data instead of from the previously collected training data.

Figure 4:
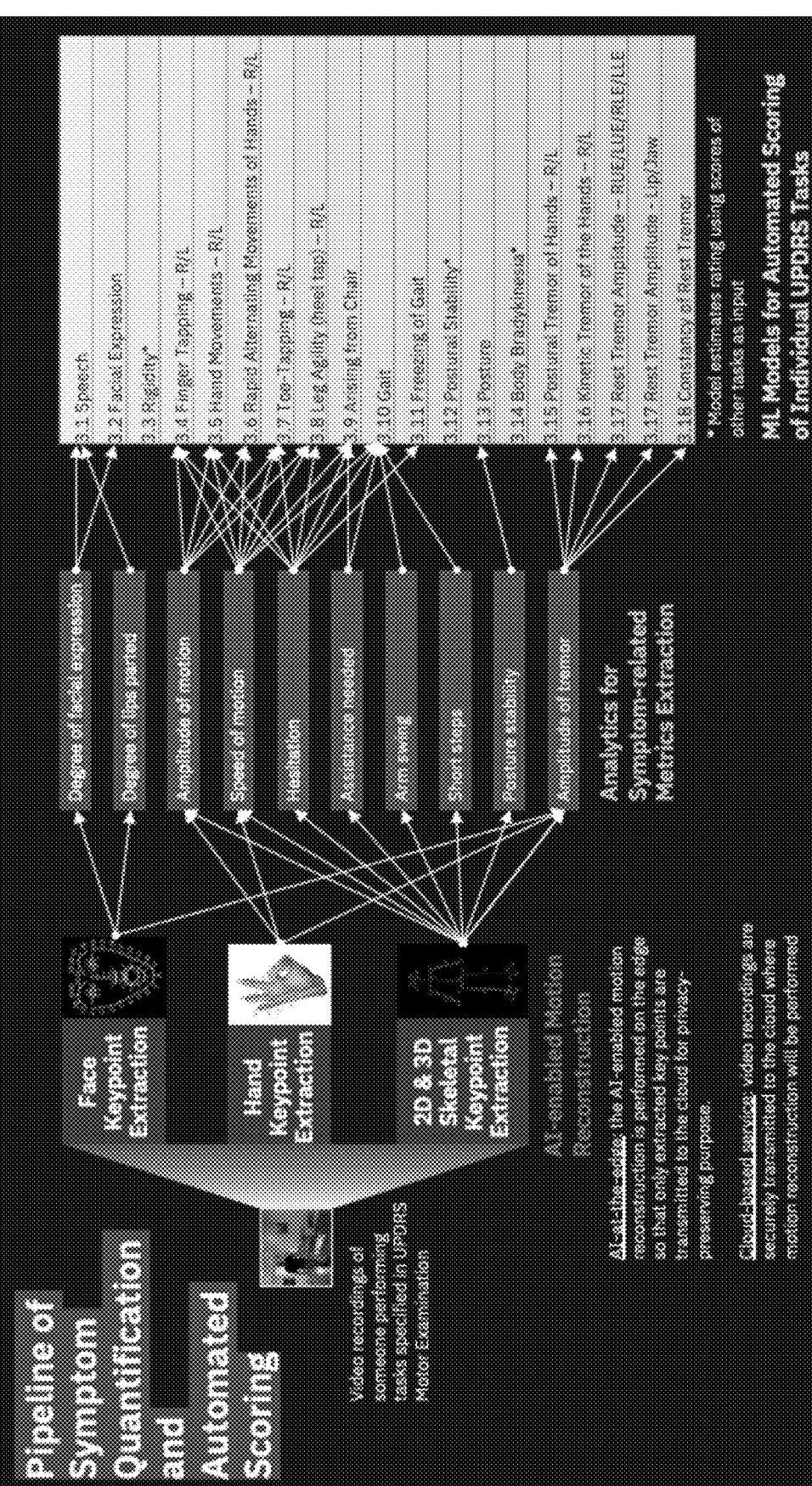
FIG. 4-7 depict exemplary flowcharts illustrating the operations of a Parkinson's symptoms assessor 134 of the Parkinson's symptoms system 100 in collecting data, extracting features from the collected data, and applying models to the extracted features to make Parkinson's symptoms assessments, in accordance with the exemplary embodiments.
Figure 5:
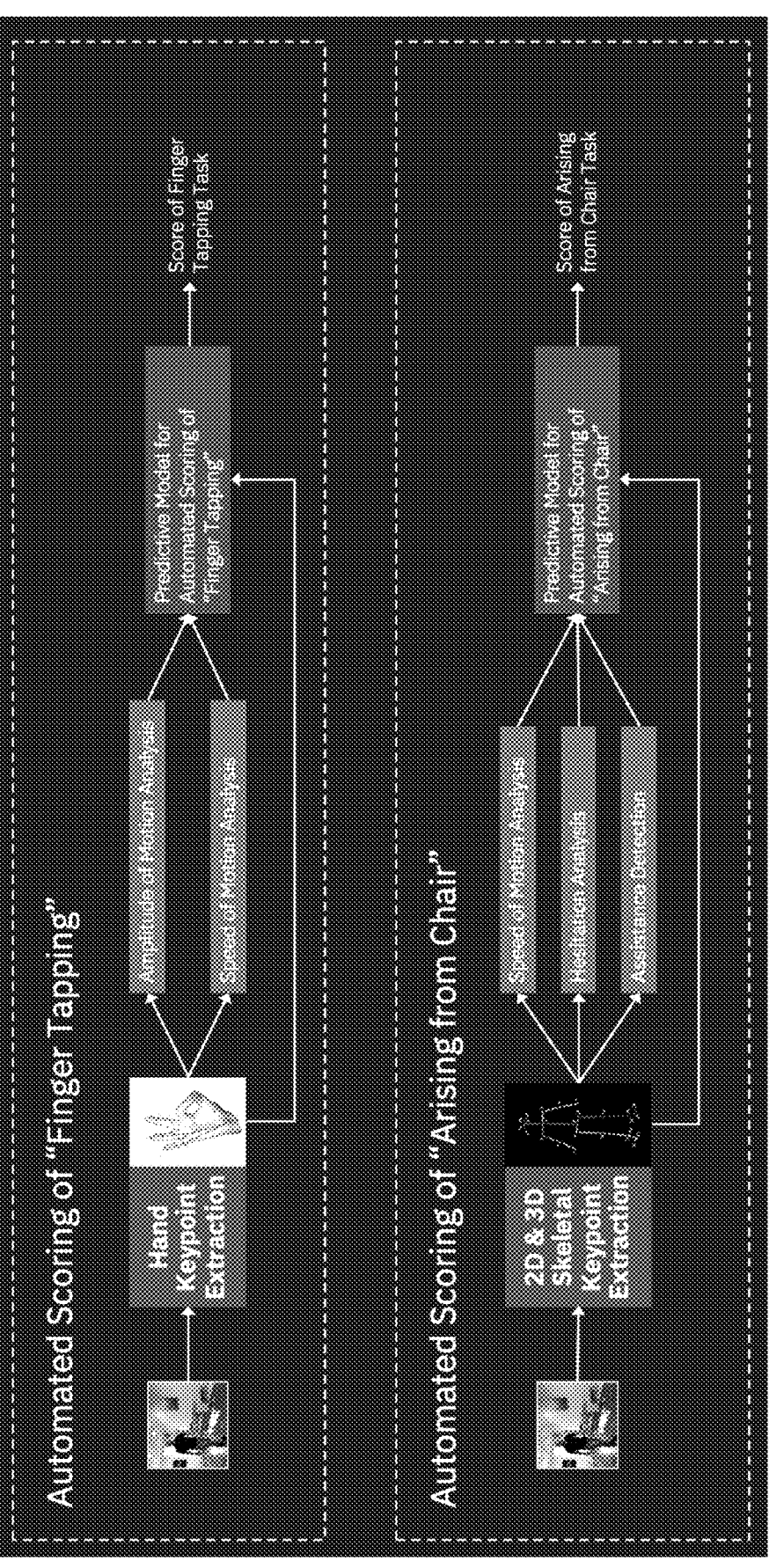

With reference to the previously introduced example where the Parkinson's symptoms assessor 134 collects user data from the sensors 110 of the user moving their face, hands, shoulders, elbows, hips, knees, and ankles, and additionally with reference to FIG. 4, the Parkinson's symptoms assessor 134 extracts the features listed in Table 1 below.

TABLE 1

| Extracted Features | |
|---|---|
| degree of facial expression | low |
| degree of lips parted | high |
| amplitude of motion | medium |
| speed of motion | low |
| hesitation | high |
| assistance needed | medium |
| arm swing | high |
| short steps | medium |
| posture stability | low |
| amplitude of tremor | high |

The Parkinson's symptoms assessor 134 may apply one or more Parkinson's symptoms models 132 to assess a user's Parkinson's disease symptoms (step 216). In embodiments, the Parkinson's symptoms models 132 may be applied to one or more extracted features to compute one or more assessment of one or more Parkinson's disease symptoms of a user, such as speech, facial expression, rigidity, finger tapping, hand movements, rapid alternating movements of hands, toe tapping, leg agility, arising from chair, gait, freezing of gait, postural stability, posture, body bradykinesia, postural tremor of hands, kinetic tremor of hands, rest tremor amplitude of extremities, rest tremor amplitude of lip and jaw, constancy of tremor, etc. As previously mentioned, such symptom assessments may be on the UPDRS of 0-4, and may be based on one or more extracted features including degree of facial expression, degree of lips parted, amplitude of motion, speed of motion, hesitation, assistance needed, arm swing, short steps, posture stability, amplitude of tremor, etc. The one or more Parkinson's symptoms models 132 may be generated through machine learning techniques such as neural networks, and the Parkinson's symptoms assessor 134 may weight the extracted features such that features shown to have a greater correlation with a correct assessment of one or more Parkinson's disease symptoms are weighted greater than those features that are not.

With reference again to the previously introduced example where the Parkinson's symptoms assessor 134 extracts features from the collected user data, the Parkinson's symptoms assessor 134 applies the trained models to assess the user's symptoms according to UPDRS as reflected in Table 2 below.

TABLE 2

Parkinson's Disease Symptoms Assessments

| | |
|---|---|
| speech | 3 |
| facial expression | 1 |
| rigidity | 1 |
| finger tapping | 4 |
| hand movements | 3 |
| rapid alternating movements of hands | 3 |
| toe tapping | 2 |
| leg agility | 1 |
| arising from chair | 3 |
| gait | 2 |
| freezing of gait | 1 |
| postural stability | 3 |
| posture | 2 |
| body bradykinesia | 2 |
| postural tremor of hands | 4 |
| kinetic tremor of hands | 4 |
| rest tremor amplitude of extremities | 3 |
| rest tremor amplitude of lip and jaw | 3 |
| constancy of tremor | 2 |

Upon the Parkinson's symptoms assessor 134's assessment of a user's Parkinson's disease symptoms, the Parkinson's symptoms assessor 134 may notify one or more users of the Parkinson's disease symptoms assessments (step 218). In embodiments, the Parkinson's symptoms assessor 134 may notify the user and/or other users (i.e., doctor of user, medical professional of user, guardian of user, etc. as discussed in user registration of configuration). The Parkinson's symptoms assessor 134 may convey the one or more Parkinson's symptoms assessments to the user in the form of audio, video, text, or any other manner via the smart device 120 or any other device. The notification of more than one assessment of Parkinson's disease symptoms may be conveyed visually in the form of a list, ranking, chart, graph, etc. via text and/or audially via one or more integrated speakers. As previously discussed, the Parkinson's symptoms assessor 134 may notify a user according to the user preferences of configuration.

With reference again to the previously introduced example where the Parkinson's symptoms assessor 134 assesses the user's symptoms according to UPDRS, the Parkinson's symptoms assessor 134 notifies the user and the user's doctor of the user's Parkinson's disease symptoms assessments.

The Parkinson's symptoms assessor 134 may evaluate and modify the Parkinson's symptoms models 132 (step 220). In the example embodiment, the Parkinson's symptoms assessor 134 may verify whether the Parkinson's symptoms assessments were appropriate in order to provide a feedback loop for modifying the Parkinson's symptoms models 132. In embodiments, the feedback loop may simply provide a means for a user (or user's doctor, physician, medical professional, guardian, etc.) to indicate whether the assessments seemed appropriate, accurate, helpful, etc. The feedback loop indication may be triggered via a toggle switch, button, slider, etc. that may be selected by the user manually by hand using a button/touchscreen/etc., by voice, by eye movement, and the like. Based on the Parkinson's symptoms assessor 134 appropriately or inappropriately assessing Parkinson's disease symptoms, the Parkinson's symptoms assessor 134 may modify the Parkinson's symptoms models 132 relating to the assessment of various Parkinson's disease symptoms. In other embodiments, the Parkinson's symptoms assessor 134 may infer or deduce whether the assessments were appropriate. For example, the Parkinson's symptoms assessor 134 may interpret user dialogue via natural language processing to determine whether the assessments were reasonable. For example, if the user says, "That definitely isn't right," "No way" or other expressions indicative of confusion or dissatisfaction, the Parkinson's symptoms assessor 134 may infer that the assessments were inappropriate or incorrect and modify the Parkinson's symptoms models 132 accordingly. Based on feedback received in the above or any other manners, the Parkinson's symptoms assessor 134 may then modify the Parkinson's symptoms models 132 to more accurately assess Parkinson's disease symptoms.

With reference to the previously introduced example where the Parkinson's symptoms assessor 134 notifies the user and the user's doctor of the user's Parkinson's disease symptoms assessments, the user says, "That seems about right" and the Parkinson's symptoms assessor 134 modifies the Parkinson's symptoms models 132 accordingly.

FIG. 3 depicts an exemplary flowchart illustrating the operations of a Parkinson's symptoms assessor 134 of the Parkinson's symptoms system 100 in assessing Parkinson's disease symptoms, in accordance with the exemplary embodiments.

FIG. 4-7 depict exemplary flowcharts and diagrams illustrating the operations of a Parkinson's symptoms assessor 134 of the Parkinson's symptoms system 100 in collecting data, extracting features from the collected data, and applying models to the extracted features to make Parkinson's symptoms assessments, in accordance with the exemplary embodiments.

FIG. 8 depicts an exemplary flowchart illustrating the operations of a Parkinson's symptoms assessor 134 of the Parkinson's symptoms system 100 in collecting training data, extracting features from the collected training data, and training models based on the extracted features, in accordance with the exemplary embodiments.

Figure 9:
FIG. 9 depicts an exemplary block diagram depicting the hardware components of the Parkinson's symptoms system 100 of FIG. 1, in accordance with the exemplary embodiments.
Figure 9:
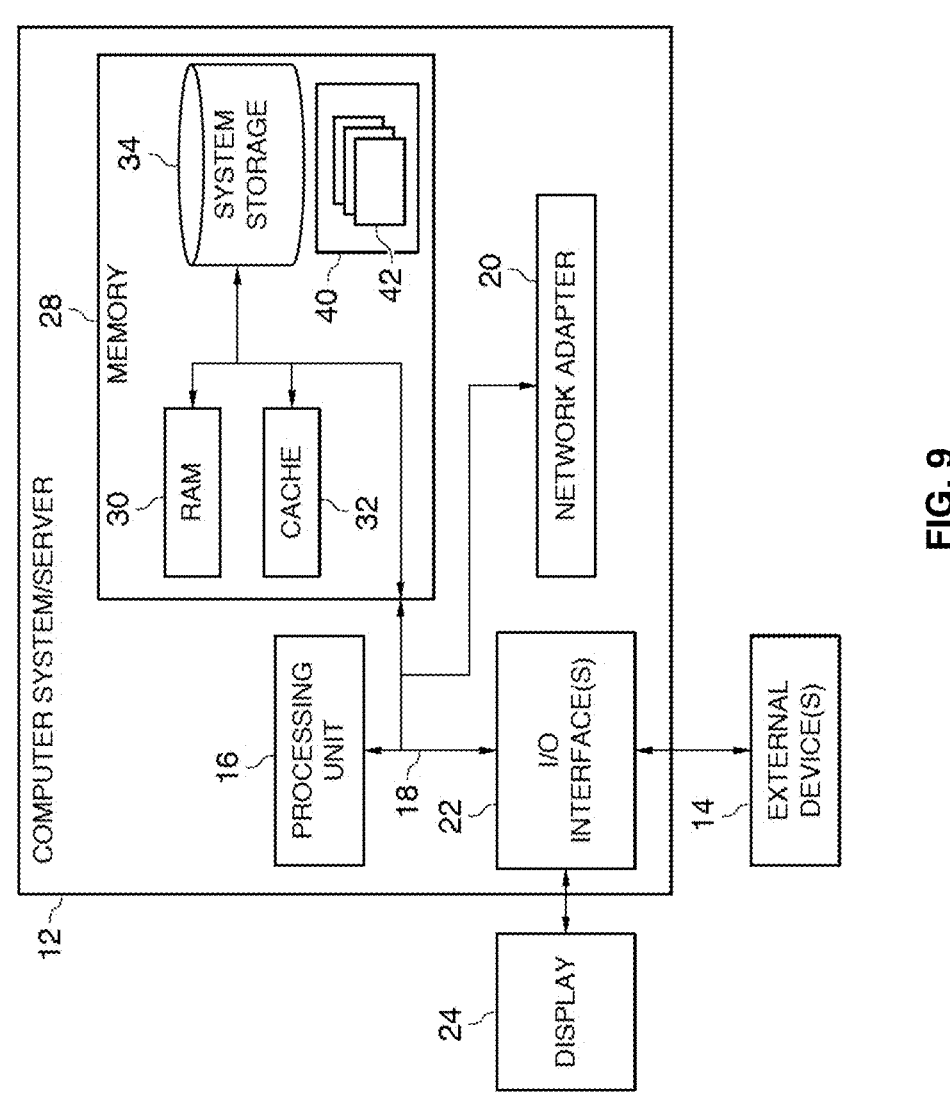

FIG. 9 depicts a block diagram of devices within the Parkinson's symptoms assessor 134 of the Parkinson's symptoms system 100 of FIG. 1, in accordance with the exemplary embodiments. It should be appreciated that FIG. 9 provides only an illustration of one implementation and does not imply any limitations with regard to the environments in which different embodiments may be implemented. Many modifications to the depicted environment may be made.

Devices used herein may include one or more processors 02, one or more computer-readable RAMs 04, one or more computer-readable ROMs 06, one or more computer readable storage media 08, device drivers 12, read/write drive or interface 14, network adapter or interface 16, all interconnected over a communications fabric 18. Communications fabric 18 may be implemented with any architecture designed for passing data and/or control information between processors (such as microprocessors, communications and network processors, etc.), system memory, peripheral devices, and any other hardware components within a system.

One or more operating systems 10, and one or more application programs 11 are stored on one or more of the computer readable storage media 08 for execution by one or more of the processors 02 via one or more of the respective RAMs 04 (which typically include cache memory). In the illustrated embodiment, each of the computer readable storage media 08 may be a magnetic disk storage device of an internal hard drive, CD-ROM, DVD, memory stick, magnetic tape, magnetic disk, optical disk, a semiconductor storage device such as RAM, ROM, EPROM, flash memory or any other computer-readable tangible storage device that can store a computer program and digital information.

Devices used herein may also include a RAY drive or interface 14 to read from and write to one or more portable computer readable storage media 26. Application programs 11 on said devices may be stored on one or more of the portable computer readable storage media 26, read via the respective R/W drive or interface 14 and loaded into the respective computer readable storage media 08.

Devices used herein may also include a network adapter or interface 16, such as a TCP/IP adapter card or wireless communication adapter (such as a 4G wireless communication adapter using OFDMA technology). Application programs 11 on said computing devices may be downloaded to the computing device from an external computer or external storage device via a network (for example, the Internet, a local area network or other wide area network or wireless network) and network adapter or interface 16. From the network adapter or interface 16, the programs may be loaded onto computer readable storage media 08. The network may comprise copper wires, optical fibers, wireless transmission, routers, firewalls, switches, gateway computers and/or edge servers.

Devices used herein may also include a display screen 20, a keyboard or keypad 22, and a computer mouse or touchpad 24. Device drivers 12 interface to display screen 20 for imaging, to keyboard or keypad 22, to computer mouse or touchpad 24, and/or to display screen 20 for pressure sensing of alphanumeric character entry and user selections. The device drivers 12, RAY drive or interface 14 and network adapter or interface 16 may comprise hardware and software (stored on computer readable storage media 08 and/or ROM 06).

The programs described herein are identified based upon the application for which they are implemented in a specific one of the exemplary embodiments. However, it should be appreciated that any particular program nomenclature herein is used merely for convenience, and thus the exemplary embodiments should not be limited to use solely in any specific application identified and/or implied by such nomenclature.

Based on the foregoing, a computer system, method, and computer program product have been disclosed. However, numerous modifications and substitutions can be made without deviating from the scope of the exemplary embodiments. Therefore, the exemplary embodiments have been disclosed by way of example and not limitation.

It is to be understood that although this disclosure includes a detailed description on cloud computing, implementation of the teachings recited herein are not limited to a cloud computing environment. Rather, the exemplary embodiments are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or data center).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based email). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Figure 10:
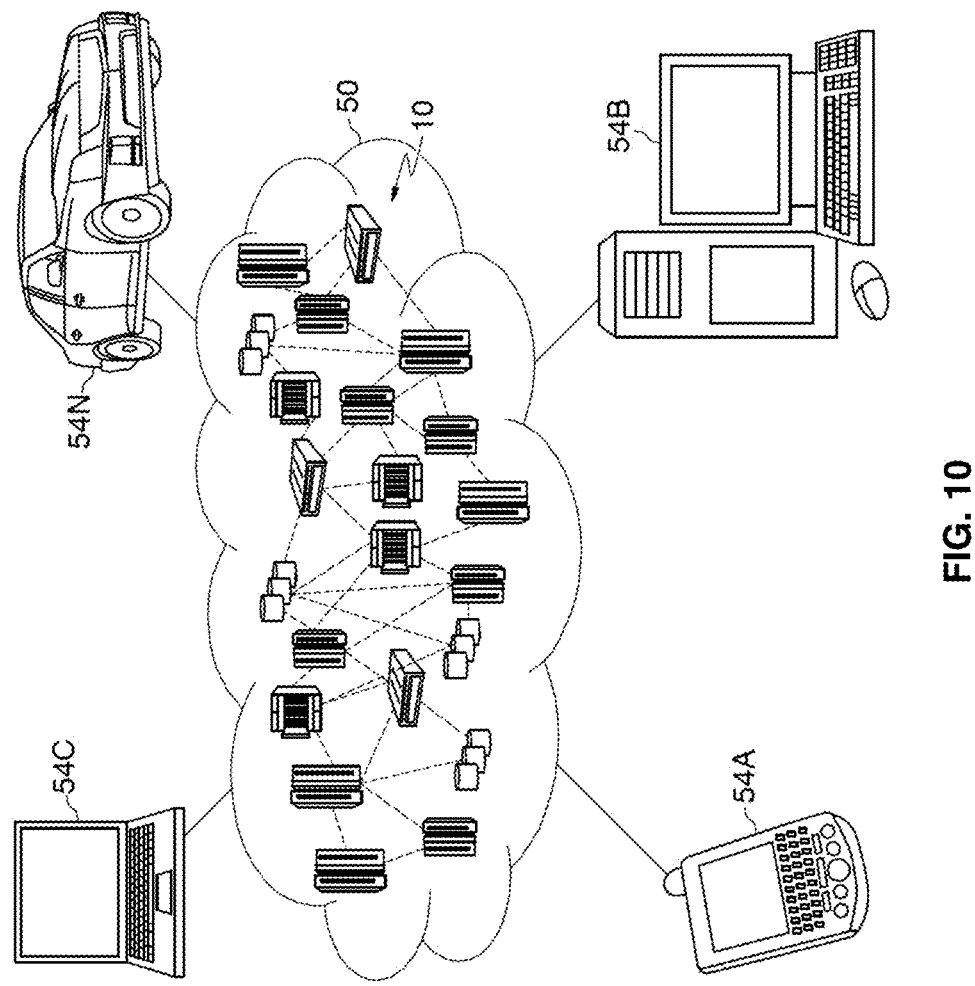
FIG. 10 depicts a cloud computing environment, in accordance with the exemplary embodiments.

Referring now to FIG. 10, illustrative cloud computing environment 50 is depicted. As shown, cloud computing environment 50 includes one or more cloud computing nodes 40 with which local computing devices used by cloud consumers, such as, for example, personal digital assistant (PDA) or cellular telephone 54A, desktop computer 54B, laptop computer 54C, and/or automobile computer system 54N may communicate. Nodes 40 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 10 are intended to be illustrative only and that computing nodes 40 and cloud computing environment 50 can communicate with any type of computerized device over any type of network and/or network addressable connection (e.g., using a web browser).

Figure 11:
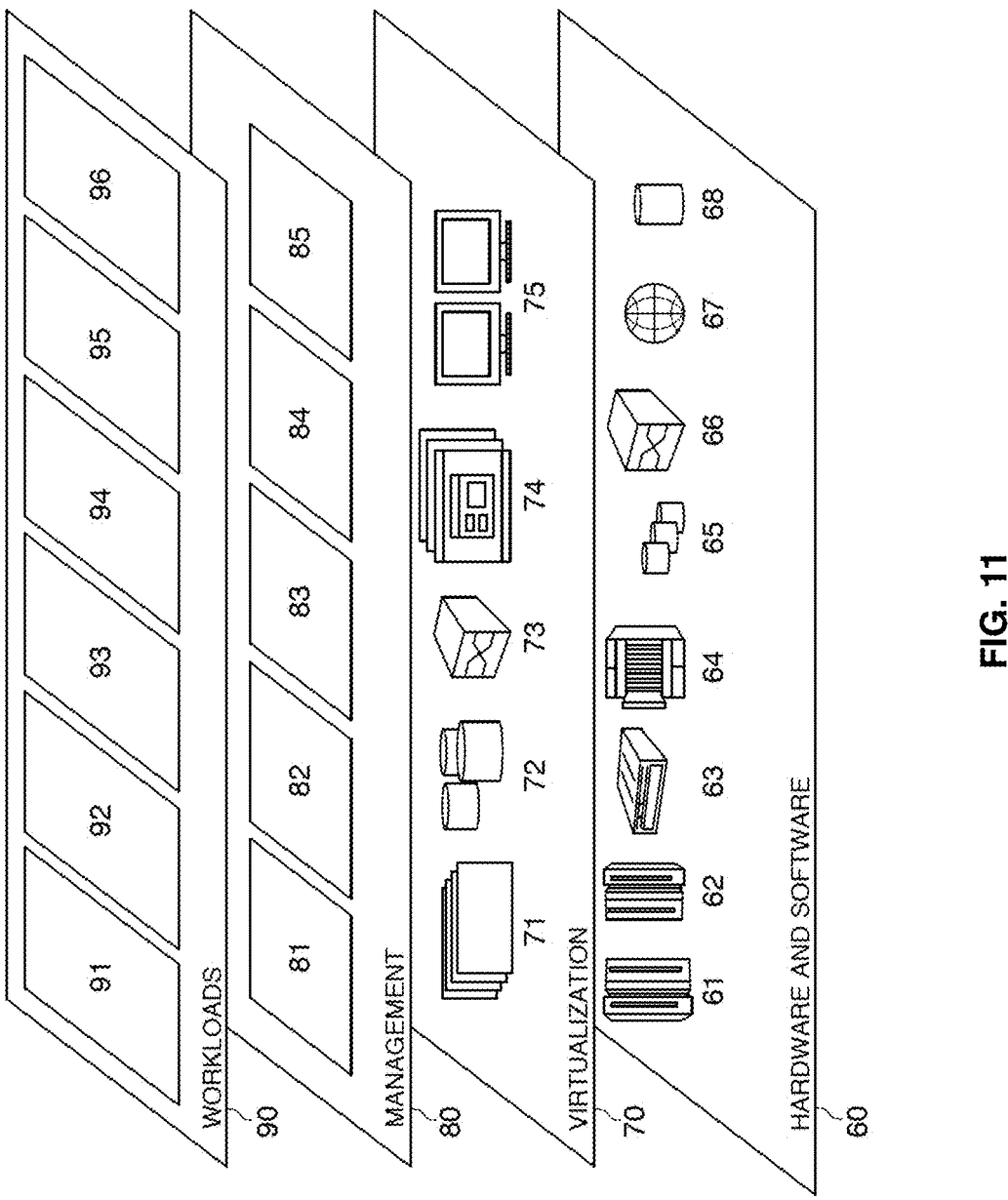
FIG. 11 depicts abstraction model layers, in accordance with the exemplary embodiments.

Referring now to FIG. 11, a set of functional abstraction layers provided by cloud computing environment 50 (FIG. 10) is shown. It should be understood in advance that the components, layers, and functions shown in FIG. 11 are intended to be illustrative only and the exemplary embodiments are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and Parkinson's disease symptoms assessment 96.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be accomplished as one step, executed concurrently, substantially concurrently, in a partially or wholly temporally overlapping manner, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

What is claimed is:

1. A computer implemented method for assessing a plurality of Parkinson's disease symptoms, the method comprising:

training a plurality of models, wherein each of the plurality of models corresponds to a different symptom of the Parkinson's disease symptoms;

collecting video data corresponding to motion of a user;

performing motion reconstruction of the user from the video data by:

identifying, by a pipeline of pre-trained deep learning neural networks, at least one of skeletal, facial, and hand key points;

generating a time series that maps movement of the key points in degrees per second within at least one of a 2D and 3D space; and smoothing the time series of the key points using linear trend fitting to remove an effect of gravity on the user;

extracting a plurality of features from the motion reconstruction; and assessing the Parkinson's disease symptoms of the user based on applying the plurality of trained models to the plurality of features.

2. The method of claim 1, further comprising:

notifying the user of the assessed Parkinson's disease symptoms; and notifying a medical professional of the user of the assessed Parkinson's disease symptoms.

3. The method of claim 1, wherein the plurality of trained models correlate the plurality of features with one or more assessments of Parkinson's disease symptoms.

4. The method of claim 1, further comprising:

receiving feedback indicative of whether the assessment of the plurality of Parkinson's disease symptoms was correct; and adjusting the plurality of models based on the received feedback.

5. The method of claim 1, the training further comprising:

collecting training data;

extracting training features from the training data; and training the plurality of models based on the extracted training features.

6. The method of claim 1, wherein assessing the plurality of Parkinson's disease symptoms of the user comprises an assessment of at least two of a user's speech, facial expression, rigidity, finger tapping, hand movements, rapid alternating movements of hands, toe tapping, leg agility, arising from chair, gait, freezing of gait, postural stability, posture, body bradykinesia, postural tremor of hands, kinetic tremor of hands, rest tremor amplitude of extremities, rest tremor amplitude of lip and jaw, and constancy of tremor.

7. The method of claim 1, wherein the plurality of features include features selected from a group comprising degree of facial expression, degree of lips parted, amplitude of motion, speed of motion, hesitation, assistance needed, arm swing, short steps, posture stability, and amplitude of tremor.

8. A computer program product for assessing a plurality of Parkinson's disease symptoms, the computer program product comprising:
one or more non-transitory computer-readable storage media and program instructions stored on the one or more non-transitory computer-readable storage media capable of performing a method, the method comprising:
training a plurality of models, wherein each of the plurality of models corresponds to a different symptom of the Parkinson's disease symptoms;
collecting video data corresponding to motion of a user;
performing motion reconstruction of the user from the video data by:
identifying, by a pipeline of pre-trained deep learning neural networks, at least one of skeletal, facial, and hand key points;
generating a time series that maps movement of the key points in degrees per second within at least one of a 2D and 3D space; and
smoothing the time series of the key points using linear trend fitting to remove an effect of gravity on the user;
extracting a plurality of features from the motion reconstruction; and
assessing the Parkinson's disease symptoms of the user based on applying the plurality of trained models to the plurality of features.

9. The computer program product of claim 8, further comprising:
notifying the user of the assessed Parkinson's disease symptoms; and
notifying a medical professional of the user of the assessed Parkinson's disease symptoms.

10. The computer program product of claim 8, wherein the plurality of trained models correlate the plurality of features with one or more assessments of Parkinson's disease symptoms.

11. The computer program product of claim 8, further comprising:
receiving feedback indicative of whether the assessment of the plurality of Parkinson's disease symptoms was correct; and
adjusting the plurality of models based on the received feedback.

12. The computer program product of claim 8, the training further comprising:
collecting training data;
extracting training features from the training data; and
training the plurality of models based on the extracted training features.

13. The computer program product of claim 8, wherein assessing the plurality of Parkinson's disease symptoms of the user comprises an assessment of at least two of a user's speech, facial expression, rigidity, finger tapping, hand movements, rapid alternating movements of hands, toe tapping, leg agility, arising from chair, gait, freezing of gait, postural stability, posture, body bradykinesia, postural tremor of hands, kinetic tremor of hands, rest tremor amplitude of extremities, rest tremor amplitude of lip and jaw, and constancy of tremor.

14. The computer program product of claim 8, wherein the plurality of features include features selected from a group comprising degree of facial expression, degree of lips parted, amplitude of motion, speed of motion, hesitation, assistance needed, arm swing, short steps, posture stability, and amplitude of tremor.

15. A computer system for assessing a plurality of Parkinson's disease symptoms, the computer system comprising:
one or more computer processors, one or more computer-readable storage media, and program instructions stored on the one or more of the computer-readable storage media for execution by at least one of the one or more processors capable of performing a method, the method comprising:
training a plurality of models, wherein each of the plurality of models corresponds to a different symptom of the Parkinson's disease symptoms;
collecting video data corresponding to motion of a user;
performing motion reconstruction of the user from the video data by:
identifying, by a pipeline of pre-trained deep learning neural networks, at least one of skeletal, facial, and hand key points;
generating a time series that maps movement of the key points in degrees per second within at least one of a 2D and 3D space; and
smoothing the time series of the key points using linear trend fitting to remove an effect of gravity on the user;
extracting a plurality of features from the motion reconstruction; and
assessing the Parkinson's disease symptoms of the user based on applying the plurality of trained models to the plurality of features.

16. The computer system of claim 15, further comprising:
notifying the user of the assessed Parkinson's disease symptoms; and
notifying a medical professional of the user of the assessed Parkinson's disease symptoms.

17. The computer system of claim 15, wherein the plurality of trained models correlate the plurality of features with one or more assessments of Parkinson's disease symptoms.

18. The computer system of claim 15, further comprising:
receiving feedback indicative of whether the assessment of the plurality of Parkinson's disease symptoms was correct; and
adjusting the plurality of models based on the received feedback.

19. The computer system of claim 15, the training further comprising:
collecting training data;
extracting training features from the training data; and
training the plurality of models based on the extracted training features.

20. The computer system of claim 15, wherein assessing the plurality of Parkinson's disease symptoms of the user comprises an assessment of at least two of a user's speech, facial expression, rigidity, finger tapping, hand movements, rapid alternating movements of hands, toe tapping, leg agility, arising from chair, gait, freezing of gait, postural stability, posture, body bradykinesia, postural tremor of hands, kinetic tremor of hands, rest tremor amplitude of extremities, rest tremor amplitude of lip and jaw, and constancy of tremor.

\* \* \* \* \*